United States Patent
Amino

[11] Patent Number: 5,152,687
[45] Date of Patent: Oct. 6, 1992

[54] COMPOSITE IMPLANT MEMBER

[75] Inventor: Hirokazu Amino, Kyoto, Japan

[73] Assignee: Kyocera Corporation, Kyoto, Japan

[21] Appl. No.: 642,705

[22] Filed: Jan. 17, 1991

Related U.S. Application Data

[63] Continuation of Ser. No. 262.892. Oct. 26. 1988. abandoned.

[30] Foreign Application Priority Data

Oct. 30, 1987 [JP] Japan .................. 62-276736

[51] Int. Cl.⁵ .............................................. A61C 8/00
[52] U.S. Cl. ..................... 433/173; 433/174; 433/176; 433/201.1
[58] Field of Search ............... 433/173, 174, 175, 176, 433/201.1

[56] References Cited

U.S. PATENT DOCUMENTS

| | | | |
|---|---|---|---|
| 3.732.621 | 5/1973 | Bostrom | 433/174 |
| 4.016.651 | 4/1977 | Kawahara et al. | 433/174 |
| 4.215.986 | 8/1980 | Riess | 433/173 |
| 4.234.309 | 11/1980 | Sellers | 433/174 X |
| 4.531.916 | 7/1985 | Scantlebury et al. | 433/173 |
| 4.560.353 | 12/1985 | Schulte et al. | 433/173 |
| 4.631.031 | 12/1986 | Richter | 433/173 |
| 4.657.510 | 4/1987 | Gittleman | 433/173 |
| 4.762.492 | 8/1988 | Nagai | 433/174 |
| 4.780.080 | 10/1988 | Haris | 433/174 X |
| 4.793.808 | 12/1988 | Kirsch | 433/173 |
| 4.950.161 | 8/1990 | Richter | 433/173 X |
| 4.964.801 | 10/1990 | Kawahara et al. | 433/173 |

FOREIGN PATENT DOCUMENTS

| | | | |
|---|---|---|---|
| 0282789 | 9/1988 | European Pat. Off. | 433/174 |
| 2717506 | 5/1978 | Fed. Rep. of Germany | 433/173 |
| 8700030 | 1/1987 | World Int. Prop. O. | 433/174 |

Primary Examiner—Gene Mancene
Assistant Examiner—Nicholas D. Lucchesi
Attorney, Agent, or Firm—Spensley Horn Jubas & Lubitz

[57] ABSTRACT

A composite implant member to be embedded both in a soft tissue and in a hard tissue comprising a ceramic soft tissue contact portion adapted to come in contact as with the skin and muscle and a metallic hard tissue contact portion adapted to come in contact as with the bone and osteoid tissue.

15 Claims, 2 Drawing Sheets

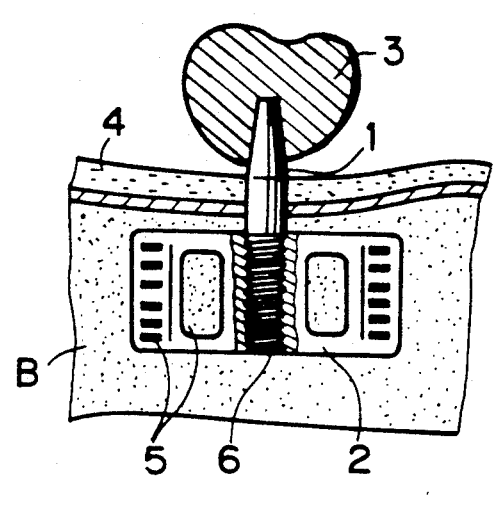
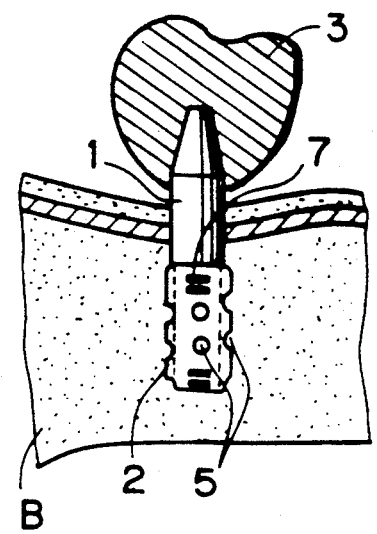
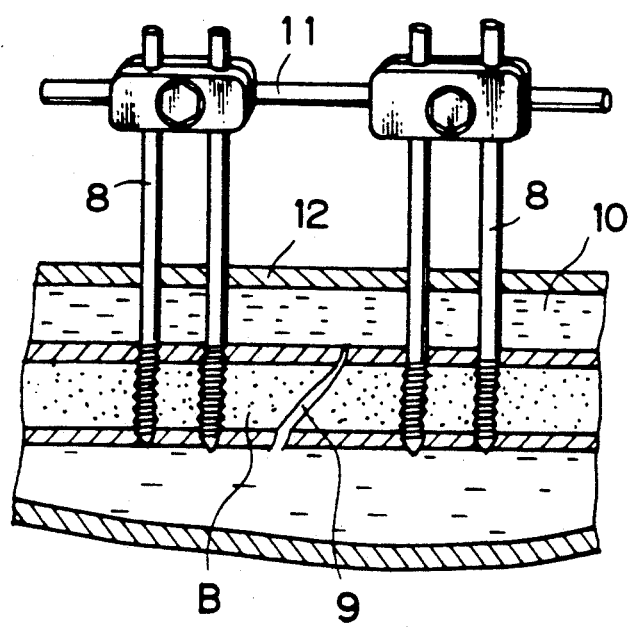
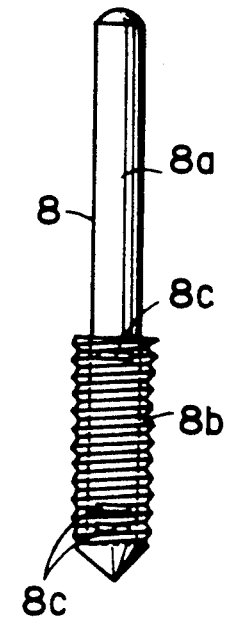

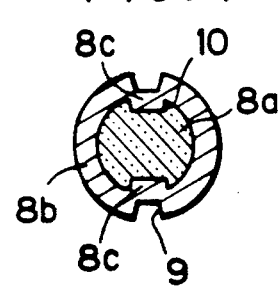
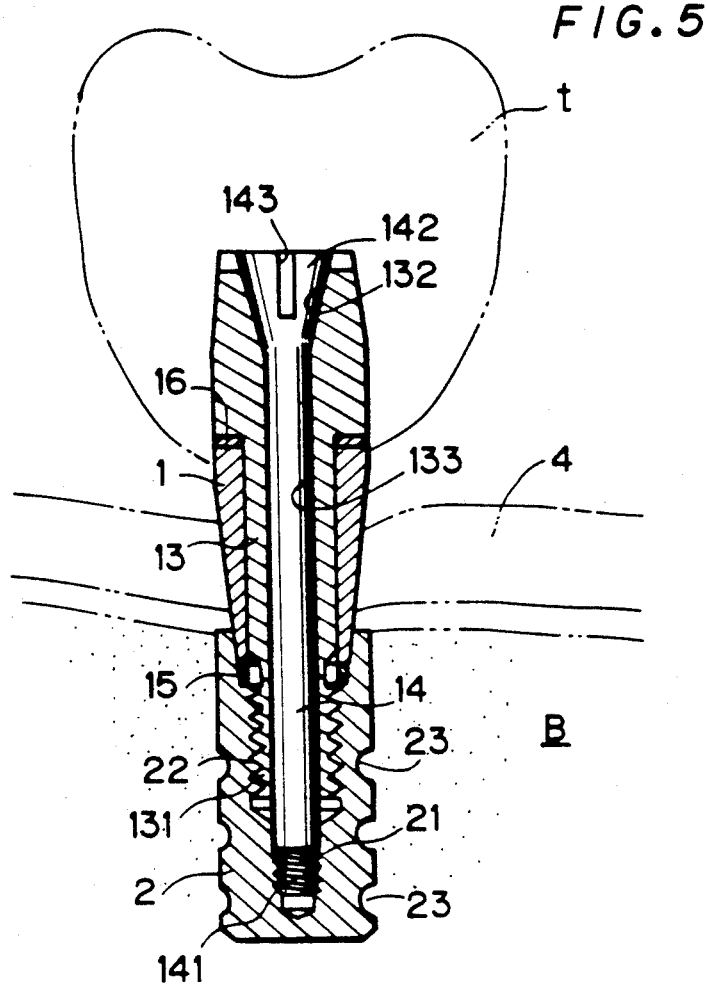
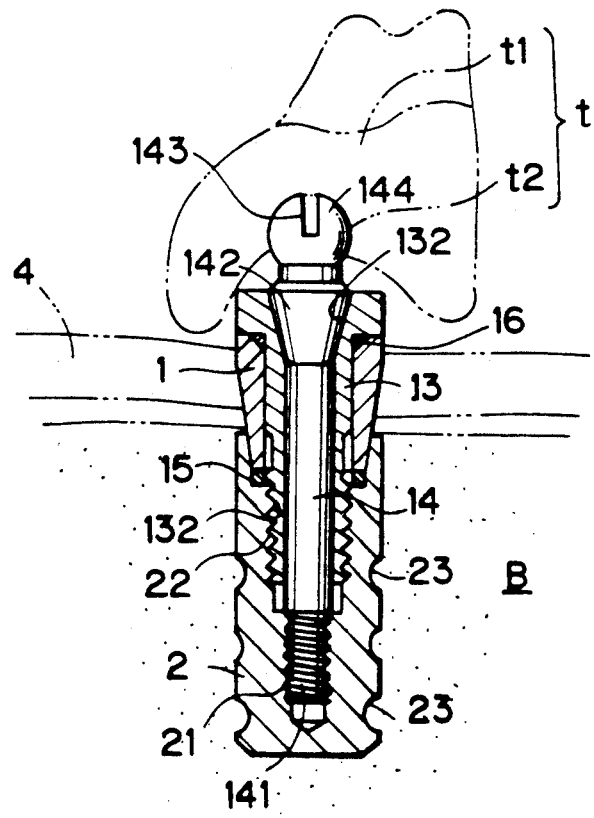

COMPOSITE IMPLANT MEMBER

This is a continuation of application Ser. No. 262,892 filed on Oct. 26, 1988, now abandoned.

BACKGROUND OF THE INVENTION

1. Field of the Invention

This invention relates to a composite implant member adapted for orthopedic, dental and cerebral surgery spheres that is not only used as an endosseous implant member for dental treatment but also used for the restoration of broken, damaged or defective bone structures by implanting the composite implant member both in a hard tissue and in a soft tissue of a living body.

2. Prior Art

The conventional type endosseous implant members as for dental treatment which are made generally of cobalt chromic alloy, titanium, titanium alloy, occasionally of platinum, platinum alloy, gold, gold alloy or stainless alloy are widely used, and the members are of such construction that a channel or hole is formed in the jaw bone, a rod-shaped or plate-shaped implant is embedded therein, and a rod-shaped post portion is caused to project from the rod-shaped or plate-shaped implant which is embedded in the bone and to extend beyond the bony tissue (soft tissue) so as to permit the mounting of an upper structure on the post portion. The portion of the implant to be embedded in the bone is formed with numerous grooves and dents and projections so as to increase an area of contact with the bone to provide stronger fixation to the bone and disperse stress. A multiplicity of vent-holes are formed in the case of the plate-shaped implant member.

In the case of a metal implant member, it is possible to bend the plate-shaped or rod-shaped metal implant in agreement with the channel and hole formed in the bone so as to provide strong initial fixation in time of implanting by making use of the characteristic properties of the metal implant. Accordingly, it is comparatively easy to deal with (modify) the metal implant. But that portion of the implant projecting outside the bone is of such construction that the metal comes in direct contact with the gum. Because the gum reacts with the metal to turn the metal blackish gray, the implant comes to be unaesthetic by lack of color harmony. In addition, because of poor compatibility of the gum with the metal, the gum portion is liable to be absorbed and inflame and makes the bone infected with various germs. Such are some of the disadvantages inherent in the conventional metal type implant member.

In recent years, an artificial dental root of ceramic and particularly that of singlecrystalline or polycrystalline alumina ceramics has come to be widely used. In the artificial dental root of the type described, there are noticed two types according to which one is that the portion of the dental root to be embedded in the bone is made of a plate-shaped metal similar to the metal implant member while the other is a dental root fixed by forming threads in the jaw bone and screwing the implant into the threaded jaw bone. It is devised to improve fixation of the implant to the bone by increasing a surface area by making thread-shaped the portion of the implant embedded in the bone or by forming holes in the portion. But formation of a groove or dents and projections raises a problem such as a great reduction in the strength of the implant and breakage of the implant. Accordingly, the artificial dental root of the type still leaves much to be improved in that it is made larger in thickness than the metal implant and made smooth in surface, resulting in smaller fixability.

Furthermore, the implant of the ceramic type has the disadvantage that also in the initial fixation of the implant, the channel to be formed in the bone must be brought into exact agreement with the implant and that the implant cannot be modified in its form as opposed to that of the metal type. But the ceramic implant is constructed such that the portion of the implant which projects outward beyond the bone makes direct contact with the gum, and in this respect the ceramic implant and the metal implant are the same. In the case of the ceramic implant and particularly in the case of a single-crystalline alumina ceramic implant, the implant, because of its colorless transparency, does not spoil the beautiful pink color of the gum and is very pleasing in appearance. In addition thereto, the ceramic implant is highly compatible with the gum, so that the gum adheres firmly to the implant and provides perfect sealing between the oral cavity and the living body (jaw bone), preventing an infective agent due to various germs invading the jaw bone.

Furthermore, that metallic implant portion which is embedded in the bone is comparatively easy to handle and accordingly, it provides strong fixation, but it poses a problem at the portion at which it extends beyond the jaw bone, namely at the portion at which it contacts the gum. On the other hand, the ceramic implant is free from any problems at the portion wherein it comes into contact with the gum outside the jaw bone, but it has the disadvantage that the portion of the implant which enters the bone becomes larger in thickness than the metal implant and is impossible of bending and cutting work. In short, the ceramic implant is difficult to handle and particularly leaves much to be discussed in point of initial fixing strength.

An implant member for orthopedic surgery is widely used as for surgical external fixation wherein a broken bone is externally fixed and held and wherein the broken bone area is fixed by an external surgical fixator. In having recourse to this means, it is contemplated to screw a long metal threaded pin through the skin into the bone and to fix the pin outside the bone to reunite the broken bone. In this case also, it poses an important problem that infection is often caused by inflammation occurring at a portion outside the bone, especially at the contacting portion between the soft tissue and the metal pin.

SUMMARY OF THE INVENTION

In an attempt to provide the most effective means for solving the problems of the type described above, the invention is intended to provide an implant member which has the characteristic properties of an implant member not only easy to handle but also excellent in fixability when the member is embedded in the bone, and in which the metal surface in contact with the bone is coated with apatite, superior in compatibility with the bone, and in which excellent bio-compatibility inherent in a ceramic material and good appearance resulting from the bio-compatibility are utilised, and which as a whole is easy to handle, strong in fixability, excellent in appearance (aesthetic) and stable in long-time use.

BRIEF DESCRIPTION OF THE DRAWINGS

A detailed description will now be given of preferred embodiments of the invention with reference to the accompanying drawings wherein:

FIGS. 1a and 1b are sectional views illustrating the state in which dental implant members of a plate type and a rod type according to the invention are embedded in an alveolar bone, respectively;

FIG. 2 is a sectional view illustrating an implant member according to the invention constructed in the form of a fixing pin for surgical exterior fixation and which is passed through the soft tissue and fixed to the bone;

FIG. 3 is a side view showing the construction in which the invention is applied to the fixing pin of FIG. 2;

FIG. 4 is a fragmentary plan view, in cross section, showing the caulked structure of the fixing pin in FIG. 3;

FIGS. 5 and 6 show still another two forms of the invention embodied in dental submersible implants wherein FIG. 5 shows an artificial tooth used as an upper structure and FIG. 6 shows a denture structure.

DETAILED DESCRIPTION OF THE INVENTION

In the embodiments of a dental implant which represents the composite implant member of the invention as shown in FIGS. 1a and 1b, the numeral designates a post portion consisting of single-crystalline or polycrystalline alumina ceramics or zirconia ceramics. The post portion 1 is screwed to a metallic hard tissue contact portion 2 made of a titanium alloy and coated on the surface with apatite powders as shown in FIG. 1a, and the post portion 1 is joined to the portion 2 by caulking the titanium alloy at a caulking portion 7, as shown in FIG. 1b. Since this metal caulking structure is the same as that shown later in FIG. 4, reference may be made to FIG. 4.

The metallic hard tissue contact portion 2 may be provided in the form of a plate as shown in FIG. 1a or in the form of a rod as shown in FIG. 1b. Formed at that portion of the contact portion 2 which is embedded in a bone B are large and small vent-holes intended to provide an anchor effect produced by the infiltration of the bone tissue through the holes 5.

An implant member is embedded in a gum portion 4 so as to come in contact with the post 1, and an upper structure 3 (an artificial tooth or the like) is mounted on the top of the post 1.

As shown in FIG. 2, in an orthopedic surgical implant member, each pair of fixing pins 8 are passed through a soft tissue 10 with a broken bone line 90 between. The pins 8 are fixed by a surgical external fixator 11 outside the soft tissue 10. As shown in FIG. 3, the pins are formed of a ceramic soft tissue contact portion 8a and a metallic hard tissue contact portion 8b of a titanium alloy, and the pin 8 is a structure joined together by caulking the contact portion 8b. An embodiment of this structure is, as shown in detail in FIG. 4, such that the metallic contact portion 8b is formed circumferentially thereof with caulking dents 9 at certain intervals, and the ceramic contact portion 8a is beforehand formed circumferentially thereof with recesses 10 in corresponding relation with the dents 9. In the state in which the contact portions 8b and 8a are fitted one into the other, the dents 9 are subjected to crimping. A tool (not shown) is used to apply force to the dents 9 to thereby deform the metal material at the dents 9 to fill the recesses 10. By so doing, the recesses 10 are filled with the metal material from the dents 9, and the two contact portions 8b and 8a are fixed both circumferentially and axially.

FIG. 5 shows another embodiment of the invention wherein the invention is used in a dental submersible implant designed to be crowned with an artificial tooth. The metallic hard tissue contact portion 2 to be implanted in the hard tissue B is a column made of a titanium alloy and having concentrical threaded holes 21 (left-handed screw) and 22 (right-handed screw). A ceramic soft tissue contact portion 1 to be combined with the contact portion 2 is a downwardly tapering sleeve and is inserted around a post sleeve 13, whose threaded portion 131 is screwed into the threaded hole 22 of the contact portion 2. The post sleeve 13 is provided on the top with a downwardly tapering hole 132 and is followed by a center bore 133. Into the center bore 133 is inserted a core member 14. When the lower threaded portion 141 of the contact portion 14 is fitted into the threaded hole 21 of the contact portion 1, the tapering portion 142 of the top of the core member 14 is fitted in tight contact into a tapering hole 132 to firmly fix the core member 14 to the post sleeve 13. The numeral 143 designates a groove for a rotary tool; 15 and 16 designate silicon washers, respectively. When, in the structure described above, an implanting operation is actually carried out, first the contact portion 2 is implanted in the jaw bone, and at the right time when the contact portion 2 has been anchored stably by the bone tissue, the contact portion 1, post sleeve 13 and core member 14 are fixed to the contact portion 2 and an artificial tooth t, which is an upper structure, is fixedly mounted on the post sleeve 13. In order to increase stability of the contact portion 2 embedded in the bone, it is desirable to form a plurality of grooves 23 in the circumference of the contact portion 2 so as to help the bone tissue make ingrowth and ossification in the grooves.

The embodiment in FIG. 6 is the same dental submersible implant as that in FIG. 5, except that a denture structure is used as an upper structure. When comparison is made with the embodiment in FIG. 5, the only difference of the FIG. 6 embodiment lies only in the top structure of the core member 14 and is substantially the same in other respects with the preceding embodiment. Accordingly, a description is given of different portions and like parts are represented by the same characters as those in FIG. 5 for simplicity's sake. The upper portion of the core member 14 projects higher than the preceding embodiment so as to fit into a corresponding mounting hole t2 in the ridge t1 of the denture structure t and forms a spherical head 144, which itself functions as a kind of post. In short, the spherical head 144 serves as a connecting post for the ridge t1.

By virtue of the structure described above, the composite implant member according to the invention has the following functions and effects.

1. The metallic hard tissue contact portion and the ceramic soft tissue contact portion can beforehand be manufactured in separate bodies, respectively, and especially the complicated work in the former's metal material is rendered possible to make it easy to devise various means for joining the material to the bone.

2. When the implant member is implanted, bone cutting may be dispensed with, an operation is facilitated and handling is greatly simplified.

3. The compatibility of the ceramic soft tissue contact portion with the soft tissue is excellent, the extraction of the implant due to infections is prevented, and long-time stability of the implant can be guaranteed.

Furthermore, the composite implant member of the invention is not only easily implanted when it is implanted in the bone but also can guarantee sealing over a long time between inside and outside the living body after its implantation with the help of excellent compatibility of the ceramic soft tissue contact portion with the soft tissue. Moreover, the implant member has an additional advantage of its excellency in appearance and has a great effect on the recovery of lost function.

I claim:

1. A composite implant member to be implanted both in a soft tissue and in a hard tissue comprising:
   a ceramic soft tissue contact post having a contact portion adapted to come in contact with a soft tissue such as skin and muscle by implantation, and an end portion;
   a metallic hard tissue contact portion adapted to come in contact with a hard tissue such as bone and osteoid tissue by implantation, said metallic hard tissue contact portion defining a bore having an internal peripheral side surface encircling the bore and adapted to receive the post end portion; and
   means for joining the end portion of the ceramic soft tissue contact post to the metallic hard tissue contact portion bore so that the post end portion engages substantially the entire perimeter of the internal peripheral side surface of the bore after the metallic hard tissue contact portion has been implanted in the hard tissue so that the ceramic post contact portion extends through the soft tissue with said end portion of the ceramic post received within the bore of the metallic hard tissue contact portion.

2. A composite implant member according to claim 1 wherein said ceramic soft tissue contact post and said metallic hard tissue contact portion have threaded mating portions for fastening the metallic portion and the ceramic post together.

3. A composite implant member according to claim 2 wherein said metallic hard tissue contact portion is a plate-shaped body and said ceramic soft tissue contact post is a screw post, said post and metallic body having threaded portions to join said post to said plate-shaped body by threaded mating, said post projecting at its upper portion higher beyond the soft tissue, said post upper portion providing a mount adapted to mount an upper structure thereon.

4. A composite implant member to be implanted both in a soft tissue and in a hard tissue comprising:
   a ceramic soft tissue contact post adapted to come in contact with a soft tissue such as skin and muscle by implantation;
   a metallic hard tissue contact portion adapted to come in contact with a hard tissue such as bone and osteoid tissue by implantation, said metallic hard tissue contact portion defining a bore; and
   means for joining one end of the ceramic soft tissue contact post to the metallic hard tissue contact portion so that the ceramic post extends through the soft tissue with said one end of the ceramic post extending to a point within the bore of the metallic hard tissue contact portion, wherein said ceramic soft tissue contact post and said metallic hard tissue contact portion are joined together by crimping the metallic contact portion relative to the ceramic contact post.

5. A composite implant member according to claim 4 wherein said metallic hard tissue contact portion is a bottomed cylindrical body having a circumferential wall and said ceramic soft tissue contact post is a cylindrical post having a recess in its circumference, said post being concentrically inserted into said bottomed cylindrical body, said cylindrical body being crimped in part of its circumferential wall relative to the recess in the circumference of said corresponding cylindrical post, said post projecting at its upper portion higher beyond the soft tissue, said upper portion providing a mount adapted to mount an upper structure thereon.

6. A composite implant member according to claim 4 wherein said metallic hard tissue contact portion is a bottomed cylindrical body having a cylindrical wall and said ceramic soft tissue contact post is a cylindrical post having a recess in its circumference, said cylindrical post being concentrically inserted into said bottomed cylindrical body, said cylindrical body being crimped in part of its cylindrical wall relative to the recess in the circumference of said corresponding cylindrical post, said bottomed cylindrical body having a threaded portion to be screwed into the hard tissue of a bone area, and said cylindrical post having an upper portion adapted to support an external fixator.

7. A composite implant member according to any of the preceding claims wherein said metallic hard tissue contact portion is selected from a group consisting pure titanium, titanium alloy, tantalum alloy, platinum, platinum alloy, gold, gold alloy, cobalt-chromic alloy and stainless steel alloy and said ceramic soft tissue contact post is selected from a group consisting singlecrystalline alumina ceramics, polycrystalline alumina ceramics and zirconia ceramics.

8. A dental composite implant comprising:
   a bioinert metal member to be embedded in a jaw bone having first and second concentrical threaded bores of a first diameter and a second diameter respectively, said first diameter being larger than said second diameter;
   a ceramic sleeve member adapted to come in contact with gum tissue, said ceramic sleeve member having an inner bore and further having one end mounted in said bioinert metal member;
   a cylindrical member for fastening said sleeve member to the metal member, said cylindrical member having a center bore therein with a downwardly tapered portion provided at its upper end, a threaded lower portion to engage said first threaded bore of said bioinert metal member, and intermediate portion to be received within the inner bore of said sleeve member, and an upper portion having a shoulder engaging the upper end of said sleeve member; and
   a core member received within the center bore of said cylindrical member for fastening said cylindrical member to the metal member, said core member having a threaded lower portion to engage said second threaded bore of said bioinert metal member, and a tapered head portion for tightly engaging said downwardly tapered bore of said center bore.

9. A dental composite implant member according to claim 8 wherein said cylindrical member comprises means for mounting a dental prosthesis thereon.

10. A dental composite implant member according to claim 8 wherein said core member comprises means for mounting thereon a dental prosthesis.

11. A dental composite implant member according to claim 8 wherein said first threaded bore and said second threaded bore of said bioinert metal member are threaded in opposite directions to each other.

12. A dental composite implant member according to claim 8 wherein said metal member has a third bore and the ceramic sleeve member has a lower peripheral end portion received within the inner periphery of the third bore provided in said metal member.

13. A method of implanting a composite implant both in a soft tissue and in a hard tissue comprising the steps of:

implanting a metallic body in a hard tissue, said metallic body defining a bore having an internal peripheral side surface encircling the bore;

allowing the hard tissue to heal; and joining one end of a ceramic post to the metallic body after the hard tissue has healed so that the ceramic post extends through the soft tissue with said one end of the ceramic post being received within the bore of the metallic body so that the post end engages substantially the entire perimeter of the internal peripheral side surface of the bore.

14. The method of claim 13 wherein the joining step further comprises joining mating threads disposed in the bore of the body and on said one end of the ceramic post.

15. The method of claim 13 wherein the ceramic post is a sleeve.

* * * * *